Oct. 12, 1971 S. McGREDY Plant Pat. 3,070
ROSE PLANT
Filed Nov. 17, 1969
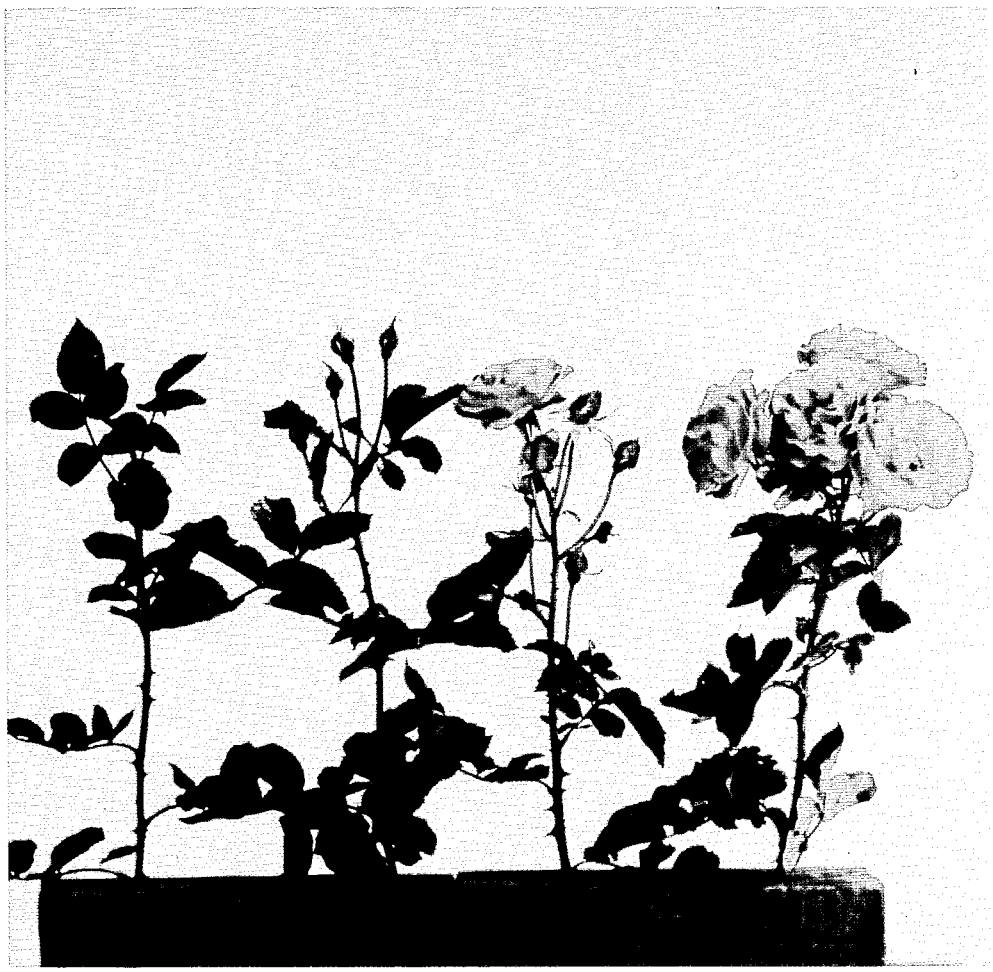

United States Patent Office

Plant Pat. 3,070
Patented Oct. 12, 1971

3,070
ROSE PLANT

Samuel McGredy, S. McGredy & Son Ltd., Portadown, Ireland

Filed Nov. 17, 1969, Ser. No. 877,535
Int. Cl. A01h *5/00*
U.S. Cl. Plt.—28 1 Claim

The invention relates to a new and distinct variety of rose plant of the floribunda class, originated by me in 1962 as a consequence of a breeding program begun in 1956. The parentage of my new rose plant is as follows: Evelyn Fison × (Circus × Korona).

The object of the cross was to produce a compact, free flowering floribunda of Evelyn Fison's brilliance without any loss of color in the flower. These objectives were achieved along with other desirable improvements, as evidenced by the following unique combination of characteristics which are outstanding in the new variety and which distinguish it from its parents as well as from all other varieties of which I am aware. My new variety is primarily characterized by: more orange than Evelyn Fison with a more compact, quick repeating plant. The older flower coloring is very similar to the bud which distinguishes it from all other orange floribundas.

Asexual reproduction of my new variety by budding, through a series of annual propagations at Santa Rosa, Calif., and Portland, Oreg., shows that all characteristics of the variety come true to form through succeeding propagations.

The accompanying photographs illustrate the primary characteristics of my new variety as nearly true as is reasonably possible to make them with presently available techniques. The color references cited are those of the Horticultural Colour Charts of the Royal Horticultural Society.

The following botanical description is based upon observation of field grown plants in Santa Rosa, Calif., and Portadown, North Ireland.

An erect, ascending shrub with slender canes and moderately branching habit. Over-all height exceeds 40 cm. at maturity with a width of 35 cm. or more. The canes diameter is 0.5–0.6 cm. or less usually, and of Fern Green (HCC 0862) color, graying with age. The armature is sparse with about 3 thorns per internode. The internodes are about 5 cm. long. The major thorns are slightly hooked, abruptly tapered, protrude about 0.9 cm. with a basal length of 0.8 cm. The small young thorns are Erythrite Red (HCC 0027) turning brownish at maturity. There are numerous scattered prickles and/or small thorns toward the blooming apex and on the peduncles.

The foliage is abundant, glossy, leathery, and odd-pinnate with 3–7 leaflets, with 5 being usual. The leaflets are ovate, serrate, glabrous, sessile and tend to be apiculate. The leaflets can be either flat or convoluted in surface depending on the climate. The overall leaf length is 12 cm. including a petiole of about 3 cm. The leaflet size is around 4.5 cm. long by 2.5 cm. wide in the apical leaflet. The petiole is ribbed and stipulate. The stipules are ciliate, scarious, persist to maturity. They are adnate about ⅓ the length of the petiole. The rhachis is similarly ribbed and has an occasional small prickle. The rhachis, petiole, and new leaflets are Fern Green (HCC 0862) with the new leaflets being shot with Oxblood Red (HCC 00823) above and Erythrite Red (HCC 0027) below. The new growth is Oxblood Red (HCC 00823). The mature leaflets are Sage Green (HCC 000861) on the upper surface and Sage Green (HCC 000861/1) anastamosed with Sage Green (HCC 000861/2) on the lower surface.

The inflorescence is in panicles of 4–10, rarely solitary. The bud opens into a flower with a depth of 2 cm. and a diameter of 4.5 cm. The bud is pointed becoming urceolate and is 1.75 cm. long by 1.5 cm. wide on the average. The bud petal color is Cardinal Red (HCC 822/2) with some Dahlia Purple (HCC 931) spotting, particularly on the guard petals. The open flower has petals that roll inward at the margins, are obovate, emarginate, crisp, velvety, imbricated. The petal size is around 3 cm. long by 3 cm. wide and number about 34 with 4 staminodia. Petal color is Orient Red (HCC 819) inside and Cherry (HCC 722) outside with Dahlia Purple (HCC 931) spots. The petal bases are small and yellow. The sepals reflex as the flower opens, are truncate, lanceolate, pubescent within and along the margins, glabrous without, modestly appendaged. The sepal color is Lettuce Green (HCC 861/3) in color with shots of Oxblood Red (HCC 00823). The disk is prominent, glabrous, yellow on its outer circumference and greenish within.

The stamens number about 138 with golden filaments and large, golden anthers with golden pollen. The pistils number about 92 with white, hairy styles and pale cream-colored stigmas.

The plant is disease and mildew resistant and has a mild attar of roses fragrance. The plant blooms essentially continuously throughout the rose season.

Having thus disclosed my invention, I claim:

1. A new and distinct variety of rose plant of the floribunda class substantially as herein shown and described primarily characterized by: the extremely free flowering compact healthy plant; the semi-double bright orange scarlet blooms carried in small trusses close to the foliage.

No references cited.

ROBERT BAGWILL, Primary Examiner